(12) United States Patent
Li et al.

(10) Patent No.: US 9,403,889 B2
(45) Date of Patent: Aug. 2, 2016

(54) DIAGNOSTIC LUNG CANCER PANEL AND METHODS FOR ITS USE

(75) Inventors: Xiao-Jun Li, Bellevue, WA (US); Paul Kearney, Montreal (CA)

(73) Assignee: Integrated Diagnostics, Inc., Seattle, WA (US)

( * ) Notice: Subject to any disclaimer, the term of this patent is extended or adjusted under 35 U.S.C. 154(b) by 316 days.

(21) Appl. No.: 13/306,823

(22) Filed: Nov. 29, 2011

(65) Prior Publication Data

US 2012/0142558 A1    Jun. 7, 2012

Related U.S. Application Data

(60) Provisional application No. 61/417,834, filed on Nov. 29, 2010.

(51) Int. Cl.
| | | |
|---|---|---|
| *C07K 14/47* | (2006.01) | |
| *G01N 27/62* | (2006.01) | |
| *G01N 33/68* | (2006.01) | |
| *G01N 33/574* | (2006.01) | |

(52) U.S. Cl.
CPC ............ *C07K 14/4748* (2013.01); *G01N 27/62* (2013.01); *G01N 33/57423* (2013.01); *G01N 33/6848* (2013.01)

(58) Field of Classification Search
None
See application file for complete search history.

(56) References Cited

U.S. PATENT DOCUMENTS

| | | |
|---|---|---|
| 2007/0099251 A1 | 5/2007 | Zhang et al. |
| 2007/0202539 A1 | 8/2007 | Aebersold et al. |
| 2007/0269895 A1 | 11/2007 | Aebersold et al. |
| 2010/0240546 A1 | 9/2010 | Lo et al. |
| 2010/0248290 A1 | 9/2010 | Lam et al. |
| 2010/0279382 A1 | 11/2010 | Aebersold et al. |
| 2010/0298404 A1 | 11/2010 | Guo et al. |

OTHER PUBLICATIONS

Patz, EF Jr. et al. Panel of serum biomarkers for the diagnosis of lung cancer. Journal of Clinical Oncology. 2007. 25(35): 5578-5583.*
Lange, V et al. Selected reaction monitoring for quantitative proteomics: a tutorial. Molecular Systems Biology. 2008. 4(222): 1-14.*
Ocak, S et al. Mass spectrometry-based proteomic profiling of lung cancer. Proc Am Thorac Soc. 2009. 6: 159-170.*
Borgia, et al. "Establishment of a multi-analyte serum biomarker panel to identify lymph node metastases in non-small cell lung cancer", *Journal of Thoracic Oncology* 2009, vol. 4, No. 3, p. 338-347.
Lehtio, et al. "Lung cancer proteomics, clinical and technological considerations", *Journal of Proteomics* Sep. 10, 2010, vol. 73, No. 10, p. 1851-1863.

\* cited by examiner

*Primary Examiner* — Renee Claytor
*Assistant Examiner* — Susan E Fernandez
(74) *Attorney, Agent, or Firm* — Cooley LLP; Ivor R. Elrifi; Matthew Pavao

(57) ABSTRACT

Disclosed herein are novel diagnostic lung cancer panels and the use of these panels to diagnose, predict, and characterize lung cancer and to monitor or predict treatment efficacy.

1 Claim, 10 Drawing Sheets

A
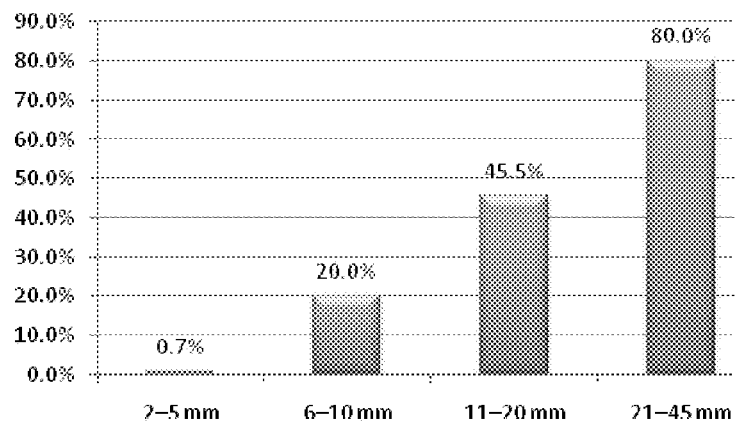
B
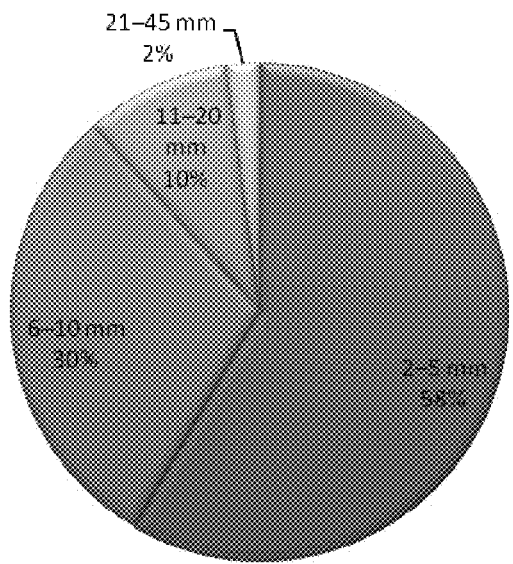
Figure 1

| Sample Type | | T1 | T2 | T3 | T4 | T5 | T6 | T7 | Number | Call by Cut off |
|---|---|---|---|---|---|---|---|---|---|---|
| Disease | 1 | X | X | X | X | X | X | X | 7 | Disease |
| Disease | 2 | X | X | X | X | X | X | X | 7 | Disease |
| Disease | 3 | X | X | X | X | X | X | X | 7 | Disease |
| Disease | 4 | X | X | X | X | X | X | X | 7 | Disease |
| Disease | 5 | X | X | X | X | X | X | X | 7 | Disease |
| Disease | 6 | X | X | X | X | X | X | X | 7 | Disease |
| Disease | 7 | X | X | X | X | X | X | X | 7 | Disease |
| Disease | 8 | X | X | X | X | X | X | X | 7 | Disease |
| Disease | 9 | X | X | X | X | X | X | O | 6 | Disease |
| Disease | 10 | X | X | X | X | X | X | O | 6 | Disease |
| Disease | 11 | X | X | X | X | X | X | O | 6 | Disease |
| Disease | 12 | X | X | X | X | X | X | O | 6 | Disease |
| Disease | 13 | X | X | X | X | X | O | O | 5 | Disease |
| Disease | 14 | X | X | X | O | X | X | O | 5 | Disease |
| Disease | 15 | X | X | O | O | X | X | O | 4 | Disease |
| Disease | 16 | X | X | X | O | O | O | X | 4 | Disease |
| Disease | 17 | X | X | X | X | O | O | O | 4 | Disease |
| Disease | 18 | X | X | X | O | O | O | X | 4 | Disease |
| Disease | 19 | X | X | X | O | O | O | O | 3 | Control |
| Disease | 20 | X | X | O | O | O | X | O | 3 | Control |
| Control | 1 | ? | X | X | X | O | O | O | 3 | Control |
| Control | 2 | ? | X | X | X | O | ? | O | 3 | Control |
| Control | 3 | ? | O | O | X | X | X | O | 3 | Control |
| Control | 4 | O | X | O | X | O | O | X | 3 | Control |
| Control | 5 | ? | O | O | X | X | X | O | 3 | Control |
| Control | 6 | ? | O | O | O | X | X | O | 2 | Control |
| Control | 7 | ? | X | O | O | O | O | X | 2 | Control |
| Control | 8 | ? | X | X | O | O | O | O | 2 | Control |
| Control | 9 | ? | X | O | O | O | O | O | 1 | Control |
| Control | 10 | ? | ? | ? | O | O | O | X | 1 | Control |
| Control | 11 | ? | O | O | O | X | O | O | 1 | Control |
| Control | 12 | ? | O | O | O | O | O | O | 0 | Control |
| Control | 13 | ? | O | O | O | ? | ? | O | 0 | Control |
| Control | 14 | ? | O | O | O | ? | ? | O | 0 | Control |
| Control | 15 | ? | O | O | O | O | O | O | 0 | Control |
| Control | 16 | ? | O | O | O | O | O | O | 0 | Control |
| Control | 17 | ? | O | O | O | O | O | O | 0 | Control |
| Control | 18 | ? | O | O | O | O | O | O | 0 | Control |
| Control | 19 | ? | O | O | O | O | O | O | 0 | Control |
| Control | 20 | O | O | O | O | O | O | O | 0 | Control |

Figure 8

C Slide 10

DIAGNOSTIC LUNG CANCER PANEL AND METHODS FOR ITS USE

CROSS-REFERENCE TO RELATED APPLICATIONS

This application claims the benefit of U.S. Provisional Patent Application No. 61/417,834, filed Nov. 29, 2010 which is incorporated herein by reference.

INCORPORATION-BY-REFERENCE OF SEQUENCE LISTING

The contents of the text file named "IDIA-002 001US v2 ST25", which was created on Aug. 13, 2014 and is 1.78 KB in size, are hereby incorporated by reference in their entireties.

BACKGROUND

One aim of modern diagnostic medicine is to better identify sensitive diagnostic methods to determine changes in health status. A variety of diagnostic assays and computational methods are used to monitor health. Improved sensitivity is an important goal of diagnostic medicine. Early diagnosis and identification of disease and changes in health status may permit earlier intervention and treatment that will produce healthier and more successful outcomes for the patient. Diagnostic markers are important for prognosis, diagnosis and monitoring disease and changes in health status. In addition, diagnostic markers are important for predicting response to treatment and selecting appropriate treatment and monitoring response to treatment.

Many diagnostic markers are identified in the blood. However, identification of appropriate diagnostic markers is challenging due to the number, complexity and variety of proteins in the blood. Distinguishing between high abundance and low abundance detectable markers requires novel methods and assays to determine the differences between normal levels of detectable markers and changes of such detectable markers that are indicative of changes in health status. The present invention provides novel compositions, methods and assays to fulfill these and other needs.

SUMMARY

In one embodiment, a diagnostic lung cancer panel is provided. The diagnostic lung cancer panel may include one or more proteins associated with lung cancer. In one embodiment, the one or more proteins associated with lung cancer may be selected from AIFM1, ALDOA, ALPL, ANPEP (or AMPN or CD13), APOE, BASP1, BST1, CCT4, CCT6A, CD14, CD163, CLU, CPB2, EEF1A1, ENO2, ENPL (or GRP94), FAM129A, FOXA2, FTH1, FTL, G6PD, HSPA5, HSPB1, ICAM3, LAMP1, LDHA, LUM, M6PRBP1, MGC2950, MMP9, NAMPT, NGAL, PCBP2, PDIA4, PKM2, PRDX1, PRDX4, PTGIS, PTPRC, PTPRJ, SCGB1A1, SLC2A3, TFRC, THY1, TUBB, TUBB2A, TYMP, UGP2, and VCP. In another embodiment, the one or more proteins associated with lung cancer may be selected from ENPL (or GRP94), NGAL, CD14, LAMP1 and ANPEP (or AMPN or CD13).

In another embodiment, the diagnostic lung cancer panel is a set of five proteins that includes ENPL (or GRP94), NGAL, CD14, LAMP1 and ANPEP (or AMPN or CD13).

In another embodiment, a diagnosis of lung cancer may be made based on the detection of differential expression or differential presence of four or more significant transitions that are associated with the lung cancer panel. The lung cancer diagnosis may be a determination of whether a lung lesion or tumor is benign or malignant.

BRIEF DESCRIPTION OF THE DRAWINGS

FIG. 1 illustrates the malignancy rate according to diameter (in mm) of the largest nodule or lesion detected by an imaging method (A) and the distribution of patients (in percent) based on the measurement of the diameter of largest nodule or lesion (B) (see Claudia I. Henschke et al for the ELCAP Group. *CT Screening for Lung Cancer: Frequency and Significance of Part-Solid and Nonsolid Nodules*. AJR: 178, May 2002, which is hereby incorporated in its entirety by reference as if fully set forth herein).

FIG. 8 illustrates the diagnosis of either lung cancer or normal or benign in samples as compared to the transition call using a cutoff of 4 or more transitions (T1-T7) present in a sample. A clinical or transition call is either "disease" (i.e., lung cancer malignancy) or "control" (i.e., benign tumor or normal tissue).

DETAILED DESCRIPTION

Figure 2:
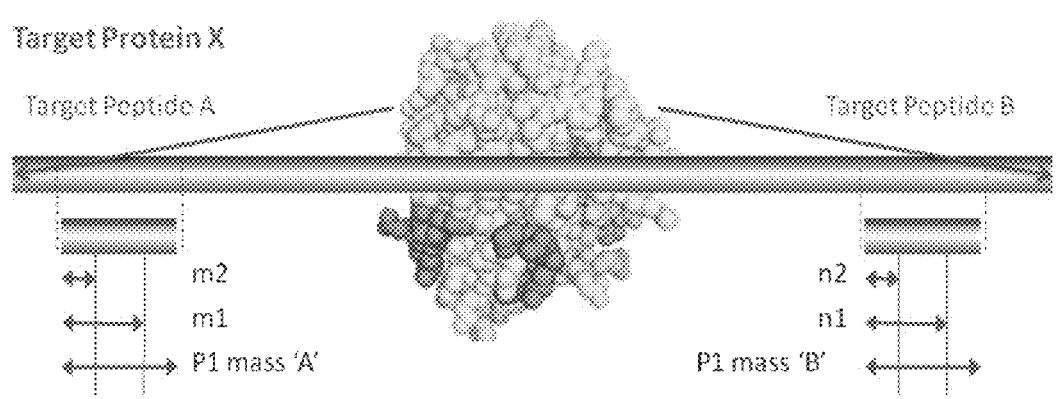
FIG. 2 is a schematic illustrating MRM technology related to the selected peptides and transitions for a target protein, Protein X.

The present disclosure provides novel compositions, methods, assays and kits directed to a diagnostic lung cancer panel. The diagnostic lung cancer panel can be used for prognosis and diagnosis, monitoring treatment and monitoring response to treatment. The diagnostic lung cancer panel may include one or more proteins associated with lung cancer.

According to some embodiments, the one or more proteins associated with lung cancer may be selected from apoptosis-inducing factor 1 (AIFM1), aldolase A (ALDOA), alkaline phosphatase (ALPL), aminopeptidase N (ANPEP or AMPN or CD13), apolipoprotein E (APOE), brain acid soluble protein 1 (BASP1), ADP-ribosyl cyclase 2 (BST1), T-complex protein 1 subunit delta (CCT4), T-complex protein 1 subunit zeta (CCT6A), cluster of differentiation 14 (CD14), cluster of differentiation 163 (CD163), clusterin (CLU), carboxypeptidase B2 (CPB2), elongation factor 1-alpha 1 (EEF1A1), enolase 2 (ENO2), endoplasmin precursor (ENPL or GRP94), protein Niban (FAM129A), forkhead box protein A2 (FOXA2), ferritin heavy chain (FTH1), ferritin light chain (FTL), glucose-6-phosphate dehydrogenase (G6PD), heat shock 70 kDa protein 5 (HSPA5), heat shock protein B1 (HSPB1), intercellular adhesion molecule 3 (ICAM3), lysosomal-associated membrane protein 1 (LAMP1), lactate dehydrogenase A (LDHA), lumican (LUM), Mannose-6-phosphate receptor binding protein 1 (M6PRBP1), pro-apoptotic caspase adaptor protein (MGC29506), matrix metalloproteinase 9 (MMP9), nicotinamide phosphoribosyltransferase (NAMPT), neutrophil gelatinase-associated lipocalin (NGAL), poly(rC)-binding protein 2 (PCBP2), protein disulfide isomerase family A-4 (PDIA4), pyruvate kinase muscle isozyme 2 (PKM2), peroxiredoxin-1 (PRDX1), peroxiredoxin-4 (PRDX4), prostaglandin 12 (prostacyclin) synthase (PTGIS), protein tyrosine phosphatase receptor type C (PTPRC), receptor-type tyrosine-protein phosphatase eta (PTPRJ), secretoglobin family 1A member 1 (SCGB1A1), solute carrier family 2 (facilitated glucose transporter), member 3 (SLC2A3), transferrin receptor protein 1 (TFRC), thymocyte differentiation antigen 1 (THY1), tubulin beta chain (TUBB), tubulin beta-2A chain (TUBB2A), thymidine phosphorylase (TYMP), UDP-glucose pyrophosphorylase 2 (UGP2) and valosin-containing protein (VCP).

In other embodiments, the one or more proteins associated with lung cancer may be selected from endoplasmin precursor (ENPL or GRP94), neutrophil gelatinase-associated lipocalin (NGAL), cluster of differentiation 14 (CD14), lysosomal-associated membrane protein 1 (LAMP1) and aminopeptidase N (ANPEP or AMPN or CD13).

In another embodiment, the diagnostic lung cancer panel is a set of five proteins that includes ENPL (or GRP94), NGAL, CD14, LAMP1 and ANPEP (or AMPN or CD13). The lung cancer panel identified herein is a sensitive and accurate diagnostic tool that can be measured in a biological sample. The lung cancer panel includes a group or set of lung cancer-specific proteins that have been associated with the disease and have been detected in biological samples of lung cancer and normal patient populations.

The diagnostic lung cancer panel of the present disclosure can be used for diagnosing lung cancer in a subject. In one embodiment, a method for differentiating between a benign or malignant lung lesion or tumor that has been visually detected by an imaging method (e.g., computed tomography (CT, positron emission tomography (PET). magnetic resonance imaging (MRI) or a combination thereof) is provided. Currently, the only reliable method for determining whether a lung lesion visualized by computed tomography (CT) is malignant is by tissue or fluid biopsy. For optimal patient outcomes, a definitive diagnosis of lung cancer is desired at the earliest stages of the disease to determine appropriate treatment. Small lesions (e.g., less than 2.0 cm) are typically not treated, but rather observed and monitored with follow up CT scans every 3-6 months to assess progression. Although this standard of care ensures that a patient is not subjected to an invasive biopsy procedure when the probability of malignancy is low (see FIG. 1A), delays detection of early stage lung cancer, thereby losing the ability to treat a cancer at a stage when treatment would likely have the greatest impact (see FIG. 1B). The lung cancer panel and methods described herein provide a diagnosis for patients with smaller lesions that are in the range of 6-10 mm, 2-5 mm or less than or equal to 2.0 cm in diameter.

In another embodiment, a method for diagnosing lung cancer via a blood test is provided. The diagnostic lung cancer panel is provides a method for diagnosing a malignant tumor based on a blood test. For example, the diagnostic lung cancer panel may be used as a screening test for subjects who are susceptible to developing lung cancer. Such a screening test may be used for smokers or those who live with a smoker, miners, or those who have been exposed to asbestos or other subjects who live or work in an environment that may put them at risk for lung cancer.

The diagnostic lung cancer panel used in the methods described herein may be used to diagnose any type of lung cancer. Examples of lung cancer that may be diagnosed using the lung cancer panel include, but are not limited to, small cell carcinoma, non-small cell carcinoma, squamous cell carcinoma, adenocarcinoma, broncho-alveolar carcinoma, mixed pulmonary carcinoma, malignant pleural mesothelioma or undifferentiated pulmonary carcinoma.

According to the methods described herein, a diagnosis of lung cancer may be made based on the detection of one or more proteins, peptides or transitions associated with the lung cancer panel that are differentially present or differentially expressed in a biological sample. The phrase "differentially present" or "differentially expressed" refers to a difference in the quantity or intensity of a marker present in a sample taken from patients having a lung cancer as compared to a comparable sample taken from patients who do not have lung cancer. For example, a protein, polypeptide or peptide is differentially expressed between the samples if the amount of the protein, polypeptide or peptide in one sample is significantly different (i.e., $p<0.05$) from the amount of the protein, polypeptide or peptide in the other sample. Further, a peptide ion transition (a "transition," described below) is differentially present between the samples if the intensity of the transition is significantly different (i.e., $p<0.05$) from the intensity of the transition in the other sample. It should be noted that if the protein, polypeptide, transition or other marker is detectable in one sample and not detectable in the other, then such a marker can be considered to be differentially present.

In one embodiment, the one or more peptides or transitions are associated with the proteins of the lung cancer panel (i.e., ENPL (or GRP94), NGAL, CD14, LAMP1 and ANPEP (or AMPN or CD13). In another embodiment, a diagnosis of lung cancer may be made based on the detection of 4 or more significant transitions in a biological sample (e.g., blood, plasma or serum). In one aspect, the 4 of more significant transitions are selected from EEEAIQLDGLDASQIR(SEQ ID NO: 1) (893.9-859.5), SYDVTSVLFR(SEQ ID NO: 2) (593.8-366.1), SYDVTSVLFR(SEQ ID NO: 2) (593.8-722.4), DVSWATGR(SEQ ID NO: 3) (446.2-677.2), GHTLTLDFTR(SEQ ID NO: 4) (580.8-966.5), GHTLTLD-FTR(SEQ ID NO: 4) (580.8-296.1) and AEFDITLIHPK (SEQ ID NO: 5) (428.8-201.1).

To increase the sensitivity of protein detection, a blood, plasma or serum sample may be initially processed to by any suitable method known in the art. In one embodiment, blood proteins may be initially processed by a glycocapture method, which enriches for glycosylated proteins, allowing quantification assays to detect proteins in the high pg/ml to low ng/ml concentration range. Example methods of glycocapture are described in detail in U.S. Pat. No. 7,183,188, issued Jun. 3, 2003; U.S. Patent Application Publication No. 2007/0099251, published May 3, 2007; U.S. Patent Application Publication No. 2007/0202539, published Aug. 30, 2007; U.S. Patent Application Publication No. 2007/0269895, published Nov. 22, 2007; and U.S. Patent Application Publication No. 2010/0279382, published Nov. 4, 2010, all of which are hereby incorporated by reference in their entirety, as if fully set forth herein. In another embodiment, blood proteins may be initially processed by a protein depletion method, which allows for detection of commonly obscured biomarkers in samples by removing abundant proteins. In one embodiment, the protein depletion method is a GenWay depletion method.

Differential expression or differential presence of the proteins of the protein panel may be measured and/or quantified by any suitable method known in the art including, but not limited to, reverse transcriptase-polymerase chain reaction (RT-PCR) methods, microarray, serial analysis of gene expression (SAGE), gene expression analysis by massively parallel signature sequencing (MPSS), immunoassays such as ELISA, immunohistochemistry (IHC), mass spectrometry (MS) methods, transcriptomics and proteomics. With respect to mass spectrometry, the most common modes of acquiring LC/MS data are: (1) Full scan acquisition resulting in the typical total ion current plot (TIC), (2) Selected Ion Monitoring (SIM) or (3) multiple reaction monitoring (MRM).

In one embodiment, differential expression or differential presence of the proteins of the panel is quantified by a mass spectrometry method. The use of mass spectrometry, in accordance with the disclosed methods and lung cancer specific panels provides information on not only the mass to charge ratio (m/z ratio) of ions generated from a sample and the relative abundance of such ions. Under standardized experimental conditions, the abundance of a noncovalent biomolecule-ligand complex ion with the ion abundance of the noncovalent complex formed between a biomolecule and a standard molecule, such as a known substrate or inhibitor is compared. Through this comparison, binding affinity of the ligand for the biomolecule, relative to the known binding of a standard molecule and the absolute binding affinity may b determined.

A variety of mass spectrometry systems can be employed for identifying and/or quantifying lung cancer biomarkers or lung cancer biomarker panels in biological samples. In some embodiments, analytes may be quantified by liquid chromatography-mass spectrometry (LC-MS) using eXtracted Ion Chromatograms (XIC). Data are collected in full MS scan mode and processed post-acquisition, to reconstruct the elution profile for the ion(s) of interest, with a given m/z value and a tolerance. XIC peak heights or peak areas are used to determine the analyte abundance.

In other embodiments, quantification of analytes is achieved by selected ion monitoring (SIM) performed on scanning mass spectrometers, by restricting the acquisition mass range around the m/z value of the ion(s) of interest. The narrower the mass range, the more specific the SIM assay. SIM experiments are more sensitive than XICs from full scans because the MS is allowed to dwell for a longer time over a small mass range of interest. Several ions within a given m/z range can be observed without any discrimination and cumulatively quantified; quantification is still performed using ion chromatograms.

In other embodiments, selected reaction monitoring (SRM) is used. SRM exploits the capabilities of triple quadrupole (QQQ) MS for quantitative analysis of an analyte. SRM is a non-scanning technique, generally performed on triple quadrupole (QQQ) instruments in which fragmentation is used as a means to increase selectivity. In SRM, the first and the third quadrupoles act as filters to specifically select predefined m/z values corresponding to the peptide ion and a specific fragment ion of the peptide, whereas the second quadrupole serves as collision cell. In SRM experiments, two mass analyzers are used as static mass filters, to monitor a particular fragment ion of a selected precursor ion. The selectivity resulting from the two filtering stages combined with the high-duty cycle results in quantitative analyses with unmatched sensitivity. The specific pair of m/z values associated with the precursor and fragment ions selected is referred to as a 'transition' (e.g., 673.5/534.3). Several such transitions (precursor/fragment ion pairs) are monitored over time, yielding a set of chromatographic traces with the retention time and signal intensity for a specific transition as coordinates.

Multiplexed SRM transitions can be measured within the same experiment on the chromatographic time scale by rapidly cycling through a series of different transitions and recording the signal of each transition as a function of elution time. The method, also referred to as multiple reaction monitoring mass spectrometry (MRM), allows for additional selectivity by monitoring the chromatographic co-elution of multiple transitions for a given analyte.

In some embodiments, an MRM-triggered MS/MS (MRM-MS/MS) method may be used to develop an MRM assay for selection and quantification of target proteins associated with lung cancer. For each target protein, several peptides are selected based on previous identification or presence in the public peptide MS/MS spectra databases TheGPM, PeptideAtlas and HUPO. The MRM-MS/MS method was developed by calculating for each peptide the precursor mass of the doubly and triply charged peptide ions and the first y fragment ion with an m/z greater than m/z (precursor)+20 Da. If these calculated transitions were observed during the MRM scan, a full MS/MS spectrum of the precursor peptide ion was acquired. The two most intense b or y fragments in the MS/MS spectrum for each peptide were recorded. Then, the two most suitable peptides for the MRM assay were selected based on observed signal intensity and origin of the peptide.

FIG. 2 is an illustration of selected peptides (Target Peptide A, Target Peptide B) having known masses (P1 mass 'A' and P1 mass 'B') and transitions (m1, m2, n1, n2) for a target protein X.

Figure 10:
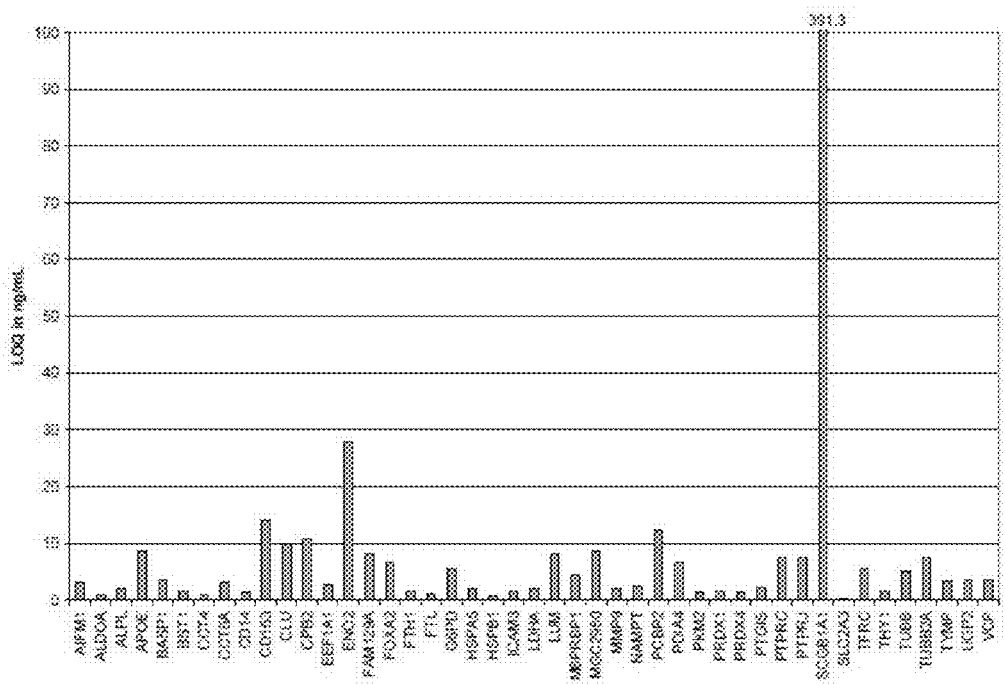
FIG. 10 is a bar graph that shows the estimated limit of quantification (LOQ) of the most intense peptide for each of a set of 45 target lung cancer related proteins: AIFM1, ALDOA, ALPL, APOE, BASP1, BST1, CCT4, CCT6A, CD14, CD163, CLU, CPB2, EEF1A1, ENO2, FAM129A, FOXA2, FTH1, FTL, G6PD, HSPA5, HSPB1, ICAM3, LDHA, LUM, M6PRBP1, MGC2950, MMP9, NAMPT, PCBP2, PDIA4, PKM2, PRDX1, PRDX4, PTGIS, PTPRC, PTPRJ, SCGB1A1, SLC2A3, TFRC, THY1, TUBB, TUBB2A, TYMP, UGP2, and VCP. The graph illustrates that the target proteins can be detected at concentrations in the ng/mL range.

Based on the peptide and transition selection described above, the MRM assay used in accordance with the methods for diagnosing lung cancer described herein measures the intensity of the four transitions that correspond to the selected peptides associated with each targeted protein. The achievable limit of quantification (LOQ) may be estimated for each peptide according to the observed signal intensities during this analysis. For example, for a set of target proteins associated with lung cancer (AIFM1, ALDOA, ALPL, APOE, BASP1, BST1, CCT4, CCT6A, CD14, CD163, CLU, CPB2, EEF1A1, ENO2, FAM129A, FOXA2, FTH1, FTL, G6PD, HSPA5, HSPB1, ICAM3, LDHA, LUM, M6PRBP1, MGC2950, MMP9, NAMPT, PCBP2, PDIA4, PKM2, PRDX1, PRDX4, PTGIS, PTPRC, PTPRJ, SCGB1A1, SLC2A3, TFRC, THY1, TUBB, TUBB2A, TYMP, UGP2 and VCP), the estimated LOQ for the most intense peptide for each lung cancer-related protein is shown in FIG. 10.

The intensity for each of the four transitions associated with the lung cancer panel were measured by MRM assay and compared between a cohort of lung cancer patient samples and a cohort of control patient samples. A control patient is either an individual who has a benign tumor or who has no known tumor tissue. An individual transition intensity in the cohort of lung cancer patient samples that is significantly different than the corresponding individual transition intensity in the cohort of control patient samples is selected as a significant transition biomarker. The protein that corresponds to the significant transition biomarker was designated as a protein in the lung cancer panel.

Figure 7:
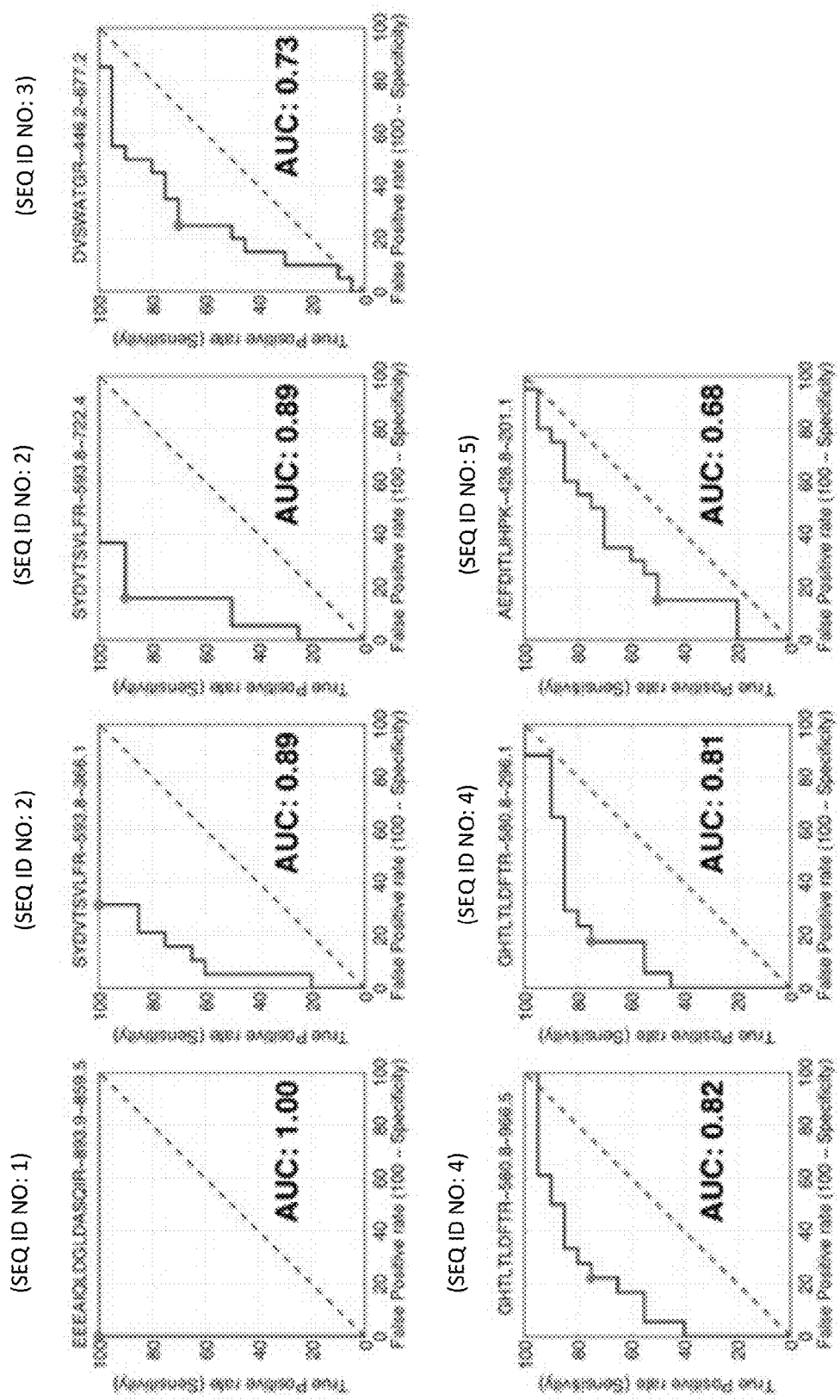
FIG. 7 is a series of receiver operating characteristic (ROC) curves illustrating the diagnostic performance for each of the following seven individual significant transitions: EEEAIQLDGLDASQIR(SEQ ID NO: 1) (893.9-859.5) (AUC=1.00), SYDVTSVLFR(SEQ ID NO: 2) (593.8-366.1)_ (AUC=0.89), SYDVTSVLFR(SEQ ID NO: 2) (593.8-722.4) (AUC=0.89), DVSWATGR(SEQ ID NO: 3) (446.2-677.2) (AUC=0.73), GHTLTLDFTR(SEQ ID NO: 4) (580.8-966.5) (AUC=0.82), GHTLTLDFTR(SEQ ID NO: 4) (580.8-296.1) (AUC=0.81) and AEFDITLIHPK(SEQ ID NO: 5) (428.8-201.1) (AUC=0.68).
Figure 9:
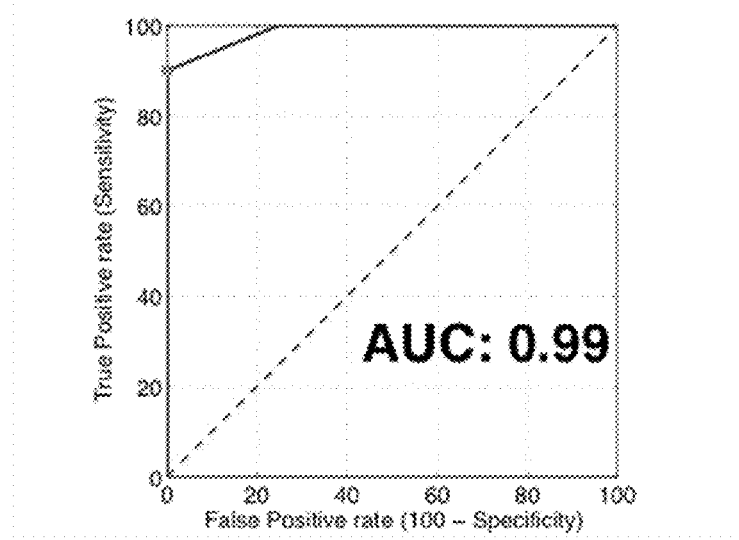
FIG. 9 is a receiver operating characteristic (ROC) curve illustrating the diagnostic performance of the multivariate lung cancer panel (AUC=0.99) as determined by the significant transitions listed in FIG. D.

To determine their diagnostic performance, a receiver operating characteristic (ROC) curve was generated for each significant transition biomarker identified above. A "receiver operating characteristic (ROC) curve" is a generalization of the set of potential combinations of sensitivity and specificity possible for predictors. A ROC curve is a plot of the true positive rate (sensitivity) against the false positive rate (1-specificity) for the different possible cut-points of a diagnostic test. FIGS. 7 and 9 are a graphical representation of the functional relationship between the distribution of a biomarker's or a panel of biomarkers' sensitivity and specificity values in a cohort of diseased subjects and in a cohort of non-diseased subjects. The area under the curve (AUC) is an overall indication of the diagnostic accuracy of (1) a biomarker or a panel of biomarkers and (2) a receiver operating characteristic (ROC) curve. AUC is determined by the "trapezoidal rule." For a given curve, the data points are connected by straight line segments, perpendiculars are erected from the abscissa to each data point, and the sum of the areas of the triangles and trapezoids so constructed is computed.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

Generation and Performance of a Lung Cancer Panel

Sample processing. A set of forty plasma samples were obtained from a cohort of lung cancer patients ("the lung cancer samples;" n=20) and a cohort of control patients ("the control samples;" n=20). The samples were processed to enrich blood glycosylated proteins using glycocapture as described above. These enriched target glycoproteins were then subjected to an MRM as discussed below.

Figure 3:
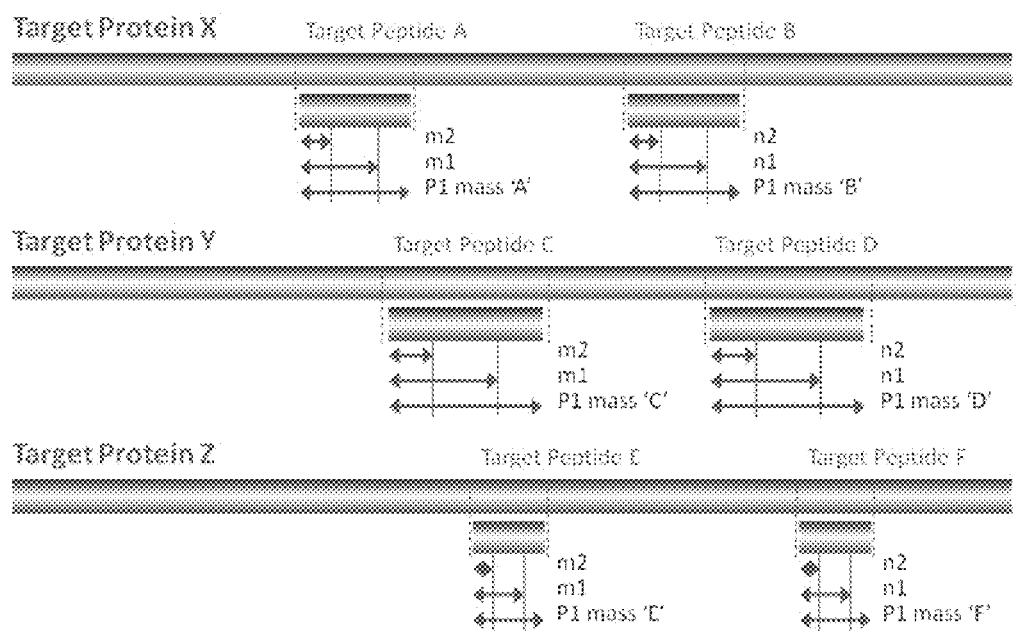
FIG. 3 is a schematic diagram illustrating selected peptides and transitions for three target proteins, Protein X, Y and Z.

MRM: selection of transition biomarkers and corresponding lung cancer panel. An MRM assay measured 1-2 target peptides with known masses and amino acid sequences (see FIG. 3, Target Peptide A, Target Peptide B, Target Peptide C, Target Peptide D, Target peptide E, Target Peptide F) for each target protein. The MRM device then searches for the known peptide masses (see FIG. 3, P1 mass 'A,' P1 mass 'B,' P1 mass 'C,' P1 mass 'ID,' P1 mass 'E,' P1 mass 'F'). When a peptide with the known peptide mass was detected, the peptide was fragmented. The MRM device measured the intensity of 2 fragments per peptide, (aka, two transitions per peptide). Thus the results of the MRM assay typically resulted in an average of 2-4 transition intensity measurements per protein (see FIG. 3, m1, m2, n1, n2).

A panel of 91 potential N-link glycoproteins was measured by MRM assay as previously described. From the 91 target glycoproteins, 148 peptides and 300 transitions were selected (each peptide had two transitions, with the exception of the peptides ESTGAQVQVAGDMLDSTER (SEQ ID NO: 6) and IDISEGNCPER (SEQ ID NO: 7), which had 4 transitions each). Three replicate MRM analyses were performed to detect presence or expression of the proteins corresponding to the transitions. A high ranking protein approach was used to determine the diagnostic importance of the detected proteins based on discovery studies and biomarkers cited in the literature (see Pubmed associations and representative references in Table 1, below.

Figure 4:
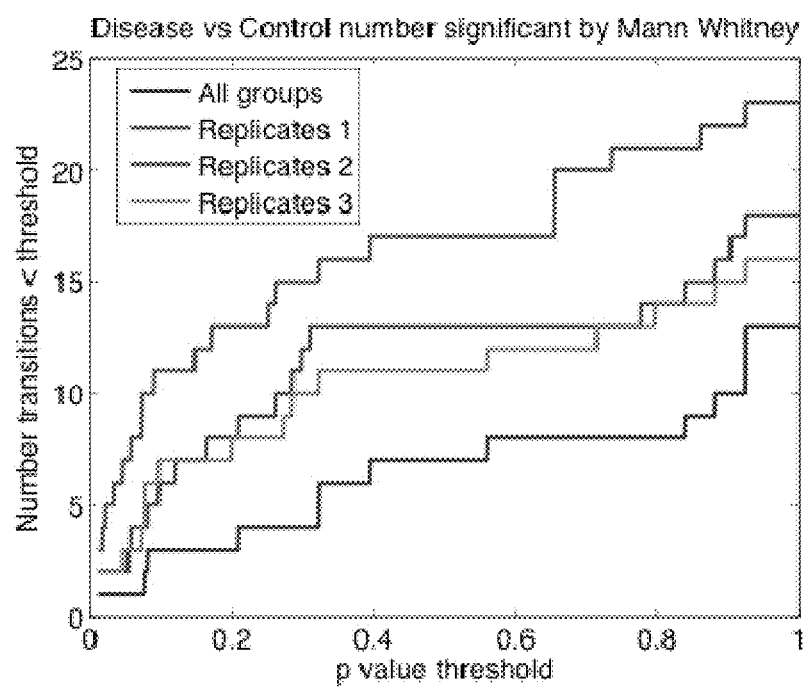
FIG. 4 is a graph illustrating the number of significant transitions that were identified in lung cancer plasma samples as compared to control plasma samples for each MRM replicate assay (Replicates 1, 2 and 3) and for all groups together. Transitions were considered significant when p was less than or equal to a threshold of 0.05.
Figure 5:
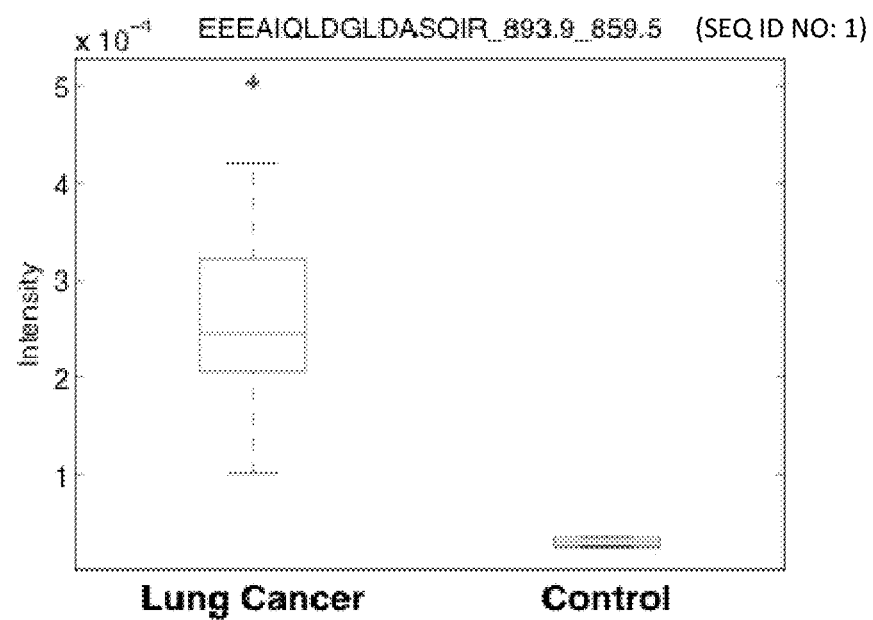
FIG. 5 is a bar graph illustrating the intensity of significant transition EEEAIQLDGLDASQIR(SEQ ID NO: 1) (893.9-859.5) in lung cancer plasma samples as compared to control samples (+p<0.05).
Figure 6A:
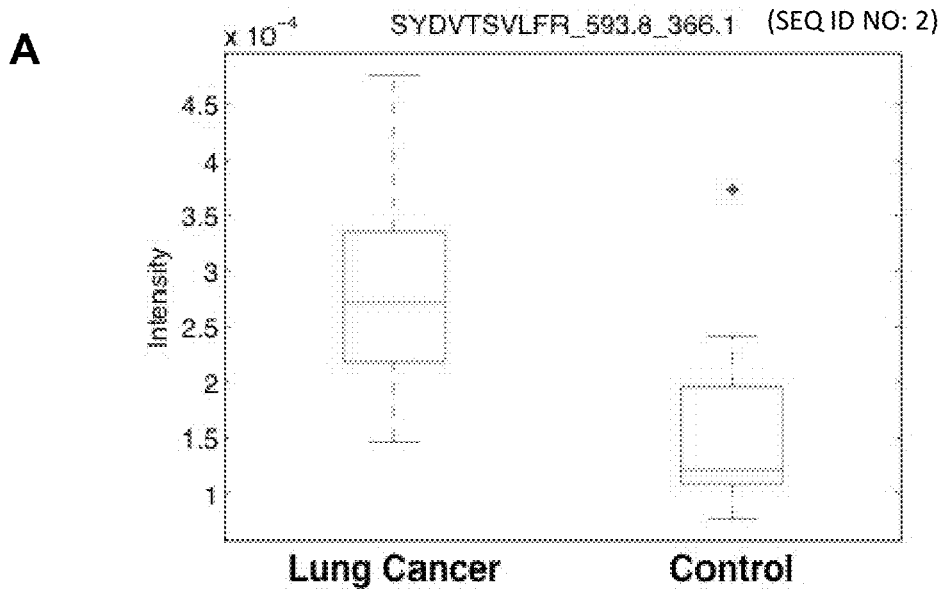
FIGS. 6A-6B are a set of box plots illustrating the intensity of significant transitions SYDVTSVLFR(SEQ ID NO: 2) (593.8-366.1) (FIG. 6A) and SYDVTSVLFR(SEQ ID NO: 2) (593.8--722.4) (FIG. 6B) in lung cancer plasma samples as compared to control samples (+p<0.05).
Figure 6B:
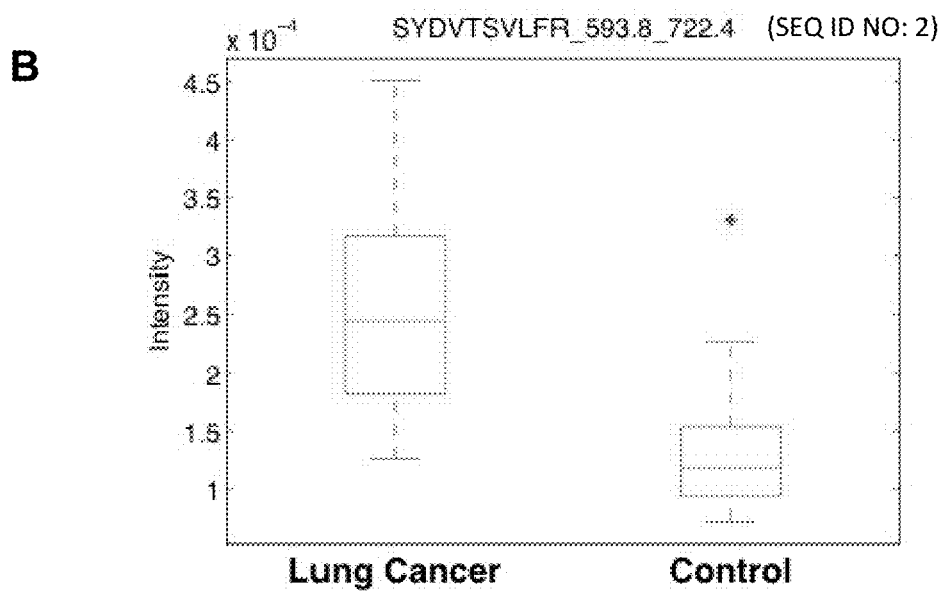

The intensities of each transition between the lung cancer samples and the control samples were compared . For each target protein, such a comparison was performed for the two transitions having the highest intensity to determine if the target protein distinguished cancerous samples from non-cancerous samples. The two highest transition intensity measurements for each target protein in the lung cancer samples were compared to the two highest transition intensity measurements for each target protein in the control samples. A transition was considered to be significant if the p value was less than 0.05 (Mann Whitney statistical analysis). Seven transitions were found to be significant (see FIG. 4), corresponding to 5 protein biomarkers. See Table 1, Significant transition intensity determinations are shown in FIG. 5 (transition EEEAIQ1LDGLDASQIR(SEQ ID NO: 1) (893.9-859.5)) and FIGS. 6A-6B (transitions SYDVTSVLFR(SEQ ID NO: 2) (593.8-366.1), (FIG. 6A) and SYDVTSVLFR (SEQ ID NO: 2) (593.8-722.4), (FIG. 6B)).

TABLE 1

Biomarkers identified using median of all replicates.

| Protein | No. of Significant Transitions | No. of Significant Peptides | No. of Pubmed Associations | Representative Reference |
|---|---|---|---|---|
| ENPL (or GRP94) | 1 | 1 | 10 | Expression of endoplasmic reticulum molecular chaperon GRP94 in human lung cancer |

TABLE 1-continued

Biomarkers identified using median of all replicates.

| Protein | No. of Significant Transitions | No. of Significant Peptides | No. of Pubmed Associations | Representative Reference |
|---|---|---|---|---|
| | | | | tissues and its clinical significance. |
| NGAL | 2 | 1 | 7 | |
| CD14 | 1 | 1 | 69 | |
| LAMP1 | 2 | 1 | 249 | Altered melanoma cell surface glycosylation mediates organ specific adhesion and metastasis via lectin receptors on the lung vascular endothelium |
| ANPEP (or AMPN or CD13) | 1 | 1 | 28 | Stromal aminopeptidase N expression: correlation with angiogenesis in non-small-cell lung cancer. |

Significant transition diagnostic performance. Next, a receiver operating characteristic (ROC) curve was generated for each significant transition to determine its individual diagnostic performance (FIG. 7). Briefly, transition EEEAIQLDGLDASQIR(SEQ ID NO: 1) (893.9-859.5) AUC was 1.00, transition SYDVTSVLFR(SEQ ID NO: 2) (593.8-366.1) AUC was 0.89, transition SYDVTSVLFR (SEQ ID NO: 2) (593.8-722.4) AUC was 0.89, transition DVSWATGR(SEQ ID NO: 3) (446.2-677.2) AUC was 0.73, transition GHTLTLDFTR(SEQ ID NO: 4) (580.8-966.5) AUC was 0.82, transition GHTLTLDFTR(SEQ ID NO: 4) (580.8--296.1) AUC was 0.81 and transition AEFDITLIHPK (SEQ ID NO: 5) (428.8--201.1) AUC was 0.68.

The combination of the identified five proteins of the lung cancer panel (as measured by the 7 transitions) was analyzed. A diagnostic call of "disease" or "neoplastic" or "malignant" or "cancerous" was made based on a cutoff of 4 or more out of the 7 individual transitions present in a blood sample. Samples having 3 or fewer out of the 7 individual transitions were diagnosed as "control" or "benign" or "not cancerous." Forty samples were analyzed and 38 were correctly diagnosed (see FIG. 8). As shown in the corresponding ROC (FIG. 9), the AUC was 0.99. The sensitivity of the 5-protein biomarker panel using the cutoff of 4 or more individual transitions present in the sample was 90% [68.3%-98.8%] and the specificity was 100% [83.2%-100%], both with a 95% confidence interval using a binomial test. These results illustrate that the combined performance of the proteins and transitions is greater than the individual markers.

The invention claimed is:

1. A compostion comprising at least four fragment ions each fragment ion having a corresponding m/z and a corresponding precursor ion with a corresponding m/z, wherein each fragment ion and the corresponding precursor ion form a transition ion pair selected from the group consisting of precursor EEEAIQLDGLDASQIR (SEQ ID NO: 1) transition pair 893.9-859.5, precursor SYDVTSVLFR (SEQ ID NO: 2) transition pair 593.8-366.1, precursor DVSWATGR (SEQ ID NO: 3) transition pair 446.2-677.2, precursor GHTLTLDFTR (SEQ ID NO: 4) transition pair 580.8-966.5, precursor GHTLTLDFTR (SEQ ID NO: 4) transition pair 580.8-296.1, and precursor AEFDITLIHPK (SEQ ID NO: 5) transition pair 428.8-201.1.

* * * * *

SEQUENCE LISTING

```
<160> NUMBER OF SEQ ID NOS: 7

<210> SEQ ID NO 1
<211> LENGTH: 16
<212> TYPE: PRT
<213> ORGANISM: Artificial Sequence
<220> FEATURE:
<223> OTHER INFORMATION: Homo sapiens

<400> SEQUENCE: 1

Glu Glu Glu Ala Ile Gln Leu Asp Gly Leu Asp Ala Ser Gln Ile Arg
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Homo sapiens

<400> SEQUENCE: 2

Ser Tyr Asp Val Thr Ser Val Leu Phe Arg
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Homo sapiens
```

```
<400> SEQUENCE: 3

Asp Val Ser Trp Ala Thr Gly Arg
1               5

<210> SEQ ID NO 4
<211> LENGTH: 10
<212> TYPE: PRT
<213> ORGANISM: Artificial Sequence
<220> FEATURE:
<223> OTHER INFORMATION: Homo sapiens

<400> SEQUENCE: 4

Gly His Thr Leu Thr Leu Asp Phe Thr Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Homo sapiens

<400> SEQUENCE: 5

Ala Glu Phe Asp Ile Thr Leu Ile His Pro Lys
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Homo sapiens

<400> SEQUENCE: 6

Glu Ser Thr Gly Ala Gln Val Gln Val Ala Gly Asp Met Leu Asp Ser
1               5                   10                  15

Thr Glu Arg

<210> SEQ ID NO 7
<211> LENGTH: 11
<212> TYPE: PRT
<213> ORGANISM: Artificial Sequence
<220> FEATURE:
<223> OTHER INFORMATION: Homo sapiens

<400> SEQUENCE: 7

Ile Asp Ile Ser Glu Gly Asn Cys Pro Glu Arg
1               5                   10
```